(12) United States Patent
Breyta et al.

(10) Patent No.: US 12,264,225 B2
(45) Date of Patent: Apr. 1, 2025

(54) POLYESTER RECYCLING PROCESS WITH PRE-REACTION PURIFICATION

(71) Applicant: TACLOV, LLC, Armonk, NY (US)

(72) Inventors: Gregory Breyta, San Jose, CA (US); Rudy J. Wojtecki, San Jose, CA (US)

(73) Assignee: Taclov, LLC, Armonk, NY (US)

( * ) Notice: Subject to any disclaimer, the term of this patent is extended or adjusted under 35 U.S.C. 154(b) by 0 days.

(21) Appl. No.: 18/377,813

(22) Filed: Oct. 8, 2023

(65) Prior Publication Data

US 2024/0101777 A1    Mar. 28, 2024

Related U.S. Application Data

(63) Continuation of application No. 17/540,164, filed on Dec. 1, 2021, now Pat. No. 11,814,492.

(60) Provisional application No. 63/120,346, filed on Dec. 2, 2020.

(51) Int. Cl.
C08J 7/02 (2006.01)
C08J 11/26 (2006.01)

(52) U.S. Cl.
CPC ............ *C08J 7/02* (2013.01); *C08J 11/26* (2013.01); *C08J 2367/02* (2013.01)

(58) Field of Classification Search
USPC ........................................................ 521/48.5
See application file for complete search history.

(56) References Cited

U.S. PATENT DOCUMENTS

| | | | | |
|---|---|---|---|---|
| 2,280,256 | A | * | 4/1942 | Patterson ............... C08G 63/48 260/DIG. 38 |
| 3,004,061 | A | * | 10/1961 | Baer ..................... C07C 69/76 560/87 |
| 3,218,287 | A | | 11/1965 | Schmidle et al. |
| 3,284,348 | A | | 11/1966 | Hutton |
| 3,580,973 | A | * | 5/1971 | Kennedy et al. ........ C08G 2/38 528/239 |
| 3,666,791 | A | | 5/1972 | Chikawa et al. |
| 3,668,235 | A | | 6/1972 | Ichikawa et al. |
| 3,691,092 | A | | 9/1972 | Floria |
| 4,003,880 | A | | 1/1977 | Sidebotham et al. |
| 4,003,881 | A | | 1/1977 | Sidebotham et al. |
| 4,064,079 | A | | 12/1977 | Sidebotham et al. |
| 4,118,187 | A | | 10/1978 | Sidebotham et al. |
| 4,137,393 | A | | 1/1979 | Sidebotham et al. |
| 4,543,364 | A | | 9/1985 | Nankee et al. |
| 4,609,680 | A | | 9/1986 | Fujita et al. |
| 7,030,264 | B1 | | 4/2006 | Inada et al. |
| 7,211,193 | B2 | | 5/2007 | Inada et al. |
| 7,959,807 | B2 | | 6/2011 | Mukai |
| 9,255,194 | B2 | | 2/2016 | Allen et al. |
| 9,611,371 | B2 | | 4/2017 | Walker |
| 9,914,816 | B2 | | 3/2018 | Allen et al. |
| 2004/0182782 | A1 | | 7/2004 | Inada et al. |
| 2009/0133200 | A1 | | 5/2009 | Mukai |
| 2015/0105532 | A1 | | 4/2015 | Allen |
| 2015/0232632 | A1 | | 8/2015 | Walker |
| 2016/0060419 | A1 | | 3/2016 | Allen |
| 2017/0218162 | A1 | | 8/2017 | Walker |
| 2019/0345306 | A1 | | 11/2019 | Walker |
| 2022/0169809 | A1 | | 6/2022 | Breyta |

FOREIGN PATENT DOCUMENTS

| | | |
|---|---|---|
| CN | 103930395 A | 7/2014 |
| CN | 108395373 A | 8/2018 |
| CN | 111690169 A | 9/2020 |
| CN | 112341315 A | 2/2021 |
| TW | 200724576 A | 7/2007 |
| WO | 2021032826 A1 | 2/2021 |
| WO | 2022118242 A1 | 6/2022 |

OTHER PUBLICATIONS

Office Action Response to Rule 161(1) dated Nov. 14, 2023, Application No. 21900191.4, IBM Patent Reference, P202008934-EP01, 31 pages.

Bashir et al., "Acetaldehyde Generation in Poly(Ethylene Terephthalate) Resins for Water Bottles", Abstract only, Journal of Macromolecular Science, Part A Pure and Applied Chemistry, vol. 39, 2002—Issue 12, 4 pages, https://doi.org/10.1081/MA-120016044.

Dubelley et al., "Water Vapor Sorption Properties of Polyethylene Terephthalate over a Wide Range of Humidity and Temperature", Abstract only, J. Phys. Chem. B 2017, 121, 8, 1953-1962, Publication Date: Jan. 25, 2017, 8 pages, <https://doi.org/10.1021/acs.jpcb.6b11700>.

IBM Patents or Patent Applications Treated as Related, Oct. 8, 2023 (pp. 1-2).

International Search Report and Written Opinion for the counterpart PCT Applicatoin No. PCT/IB2021/061238 dated Mar. 9, 2022 (12 pages).

* cited by examiner

*Primary Examiner* — Terressa Boykin
(74) *Attorney, Agent, or Firm* — Kilpatrick Townsend & Stockton LLP

(57) ABSTRACT

A depolymerization reaction of a polyester input with an organocatalyst and an alcohol solvent produces (i) a recycled monomeric or oligomeric diester from the polyester, (ii) the organocatalyst for reuse, and (iii) the alcohol solvent, which may also be reused. The presence of volatile impurities, such as water, acetyl aldehyde, and organic solvents can interfere with the success of the depolymerization reaction. A pre-reaction distillation step removes volatile impurities from the polyester input resulting in an efficient depolymerization reaction with consistency among batches. The polyester input may be further treated with a water azeotrope to remove water from the polyester input prior to the pre-reaction distillation.

18 Claims, 8 Drawing Sheets
(5 of 8 Drawing Sheet(s) Filed in Color)

POLYESTER RECYCLING PROCESS WITH PRE-REACTION PURIFICATION

TECHNICAL FIELD

The present invention relates generally to recycling processes and more specifically, to the incorporation of a distillation step to a recycling process for polyester-based materials.

BACKGROUND OF THE INVENTION

In a chemical recycling process, even very small amounts of impurities in feedstock polymers can cause significant reductions in the recycling output and on the quality of the output. Such polymer impurities (including low molecular weight volatile impurities) can cause a haze formation in an otherwise clear material or can degrade performance of packaging polymers. In food contact use, acetaldehyde (AA), which is a degradation byproduct formed when polyethylene terephthalate (PET) is heated, can alter the taste of beverages placed in bottles made from PET that have only trace amounts of AA. While strongly-flavored drinks, such as colas, can tolerate AA amounts of up to 8 ppm of AA, flavorless drinks, such as potable water, should have AA amounts less than 3 ppm. Similarly, in chemical processes, impurities carried in the inputs to a reaction can cause undesired side products to be formed. For example, materials that are processed in an uncontrolled atmosphere can pick up varying amounts of water depending on the presence of variables in the storage or processing environment, such as humidity, temperature, and types of storage. Within the context of recycling materials and reagents, both PET and ethylene glycol (EG) are hydroscopic. Although PET absorbs less than 1% water, water is often used in sorting and cleaning processes used in multi re-use recycling facilities from which the PET used in chemical recycling is sourced. The presence of this water in a PET input can reduce the efficiency and effectiveness of a PET chemical recycling process.

SUMMARY OF THE INVENTION

In one aspect, the present invention relates to a method comprising: treating a material comprising a polyester with distillation to remove volatile impurities from the material; depolymerizing the distilled material with an organocatalyst and an alcohol solvent; and recovering reaction products from the depolymerization comprising a monomeric or oligomeric diester from the polyester, the organocatalyst for reuse, and the alcohol solvent as an unreacted by-product of the depolymerization.

In another aspect, the present invention relates to a method comprising: removing water from a material comprising a polyester by treating the material with a solvent that forms an azeotrope with water; treating the material with distillation to remove volatile impurities from the material; depolymerizing the distilled material with an organocatalyst and an alcohol solvent; and recovering reaction products from the depolymerization comprising a monomeric or oligomeric diester from the polyester, the organocatalyst for reuse, and the alcohol solvent as an unreacted by-product of the depolymerization.

In a further embodiment, the present invention relates to a method comprising: treating a material comprising a polyethylene terephthalate (PET) with a distillation process to remove volatile impurities from the material; depolymerizing the distilled material with an amine organocatalyst and/or carboxylic acid salt of same and an alcohol solvent; and recovering reaction products from the depolymerization comprising bis(2-hydroxyethyl)terephthalate (BHET) as a monomeric diester of the PET, the amine organocatalyst for reuse, and any excess alcohol solvent.

Additional aspects and/or embodiments of the invention will be provided, without limitation, in the detailed description of the invention that is set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A is the stacked NMR spectra of the water and EG content and FIG. 4B is a graph showing the mole fraction water and EG content in the distillates.

DETAILED DESCRIPTION OF THE INVENTION

Figure 1:
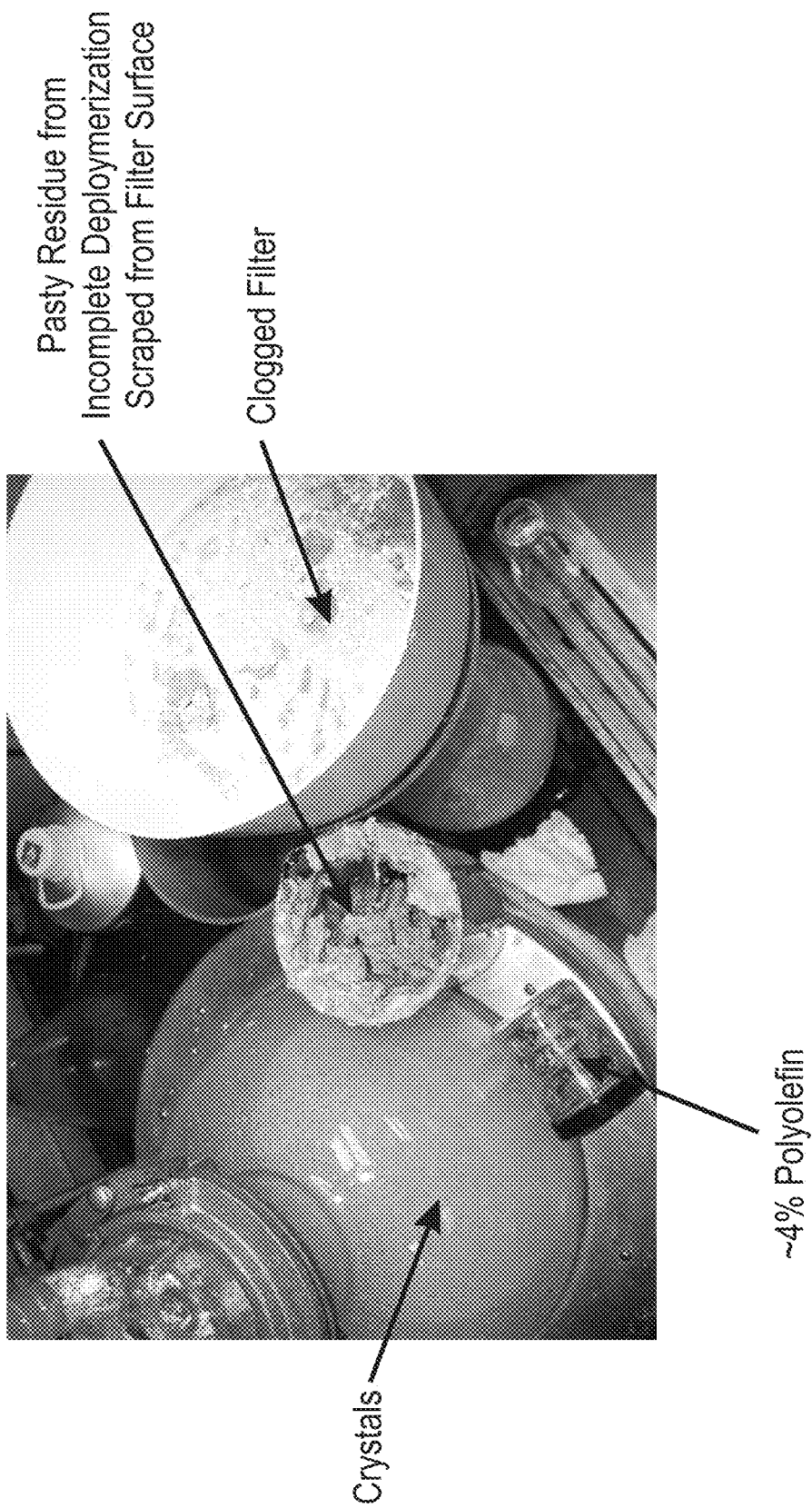
FIG. 1 is a photograph showing the results of a depolymerization reaction carried out with water contaminated PET input without pre-reaction distillation (Example 1).

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

The volatile catalyst (VolCat) chemical recycling process is described in U.S. Pat. No. 9,255,194 B2 to Allen et al. and U.S. Pat. No. 9,914,816 B2 to Allen et al. In one embodiment, the VolCat process depolymerizes polyester with an alcohol solvent and an organocatalyst in a reactor at a temperature at or higher than the boiling point of the alcohol. In another embodiment, the organocatalyst has a boiling point at least 50° C. lower than the boiling point of the alcohol solvent and the depolymerization is run at a temperature higher than the boiling point of the alcohol solvent.

In a further embodiment, the organocatalyst has a boiling point at least 50° C. lower than the boiling point of the alcohol solvent and the depolymerization is run at a temperature higher than the boiling point of the organocatalyst. In another embodiment, the polyester input and the alcohol solvent are heated to a reaction temperature of about 200-250° C. prior to the introduction of the organocatalyst. Reaction products from the VolCat depolymerization are monomeric and/or oligomeric diesters from the polyester as well as recovered organocatalyst and excess alcohol solvent, the former of which is intended for reuse into recycled polyester products and the latter of which may also be reused in subsequent depolymerization reactions.

In another embodiment, the VolCat reaction is carried out in a chemical reactor, which may be a pressure reactor, such as an autoclave or extrusion reactor, or a non-pressurized reactor, such as a round bottom flask. In a further embodiment, the depolymerization reaction, which may be pressurized or non-pressurized, as well as one or more optional purification steps for the monomer product are carried out in batches and/or in a continuous flow process. In another embodiment, a solvent in which the monomer product has limited solubility may be used to purify the depolymerized polyester monomer product, whether obtained in a batch process or though continuous flow. Alcohol and/or water are non-limiting examples of such purification solvents. Where an alcohol is used for the purification, the alcohol may be the unreacted alcohol from the depolymerization reaction or a newly introduced clean alcohol. In a further embodiment, the recovered monomer product obtained from the VolCat reaction may be used to produce a new polymer material.

In another embodiment, the polyester is selected from the group consisting of polyethylene terephthalate (PET), polyethylene naphthalate (PEN), polybutylene terephthalate (PBT), polytrimethylene terephthalate (PTT), polyethylene furanoate (PEF), and combinations thereof. In a further embodiment, the alcohol solvent is a glycol and/or diol solvent. In another embodiment, the alcohol solvent is selected from the group consisting of 1,2-ethanediol (ethylene glycol, EG), 1,3-propanediol (trimethylene glycol), 1,4-butanediol (tetramethylene glycol), 1,5-pentanediol (pentylene glycol), and combinations thereof. In a further embodiment, the organocatalyst is an amine organocatalyst and/or carboxylic salt of same. In another embodiment, the amine of the amine organocatalyst and/or carboxylic acid salt of same is a tertiary amine. In a further embodiment, the amine organocatalyst and/or carboxylic acid salt of same is selected from the group consisting of triethylamine (TEA), tetramethylethylenediamine (TMEDA), pentamethyldiethylenetriamine (PMDETA), trimethyl triaza cyclononane (TACN), 4-(N,N-dimethylamino)pyridine (DMAP), 1,4-diazabicyclo [2.2.2]octane (DABCO), N-methyl imidazole (NMI), and combinations thereof. In another embodiment, the amine organocatalyst and/or carboxylic acid salt of same is TEA and/or a carboxylic acid salt of same.

In one embodiment, the polyester input comprises a terephthalate and the recovered depolymerized reaction product comprises a terephthalate ester monomer. In another embodiment, the polyester input comprises PET and the recovered polyester monomer product is bis(2-hydroxyethyl)terephthalate (BHET). In a further embodiment, the polyester input comprises PET, the alcohol is EG, the amine organocatalyst is TEA and/or a carboxylic salt of same, and the recovered reaction products comprise unreacted EG, the TEA, and BHET.

Described herein is a modified VolCat process comprising a pre-reaction distillation that is carried out during or after the heating of the polyester input and alcohol solvent just prior to the addition of the organocatalyst to the reaction mixture. The pre-reaction distillation: (i) removes volatile impurities from the polyester input; (ii) increases product purity following the completion of the VolCat process; (iii) eliminates the need for prior drying of the inputs before introduction into the reactor; and (iv) produces consistent reaction times that do not need to be adjusted between batches or during the running of a flow process.

Examples of volatile impurities that may be present in polyester inputs and which are removed by the pre-reaction distillation include, without limitation, water, acetaldehyde (AA), acetaldehyde acetals (e.g., acetaldehyde ethylene acetal), organic solvents that are used to purify the polyester inputs, other unwanted organic materials, and combinations thereof. As previously noted herein, AA is a degradation product formed when a polyester product is heated. Removal of AA early in the recycling process is an important step since AA tends to increase in content during recycling. Examples of organic solvents that may be present in the polyester inputs include, without limitation, dichloromethane (DCM), which is used to remove color from polyester inputs (FIGS. 3, 5); hexafluoro-2-propanol (HFIPA), which is used as a polyester solvent; and solvents that form azeotropes with water. In one embodiment, prior to the pre-reaction distillation, the polyester input may be treated with a solvent that forms an azeotrope with water to help scavenge residual water from the polyester input. The application of water azeotropes is particularly effective where the polyester input has >50 ppm of water. Examples of water azeotropes that may be used to treat the polyester input include, without limitation, diethyl ether, alkanes, aromatic hydrocarbons, and combinations thereof. Examples of alkanes include, without limitation, heptanes, octanes, nonanes, and decanes. Examples of aromatics hydrocarbons include, without limitation, toluene and xylenes. Such azeotropes are later removed from the polyester input by the pre-reaction distillation.

The VolCat process is designed to recycle the organocatalyst at the end of the depolymerization process. The pre-reaction distillation improves the purity of the reaction products by removing volatile impurities (such as solvents used to purify inputs) from carrying through into the reaction, where they might otherwise be entrained with the organocatalyst during its recovery. The removal of the volatile impurities early in the VolCat process eliminates or minimizes the burden on post-reaction purification steps.

With the original VolCat process, low grade polyester samples are purified in a separate unit operation by energy-intensive drying of the input material in an oven immediately prior to initiation of the reaction. The pre-reaction distillation purification step eliminates the need to oven-dry the sample and uses the already required reaction mixture heating step to advantageously distill off the undesirable volatile materials.

Figure 2:
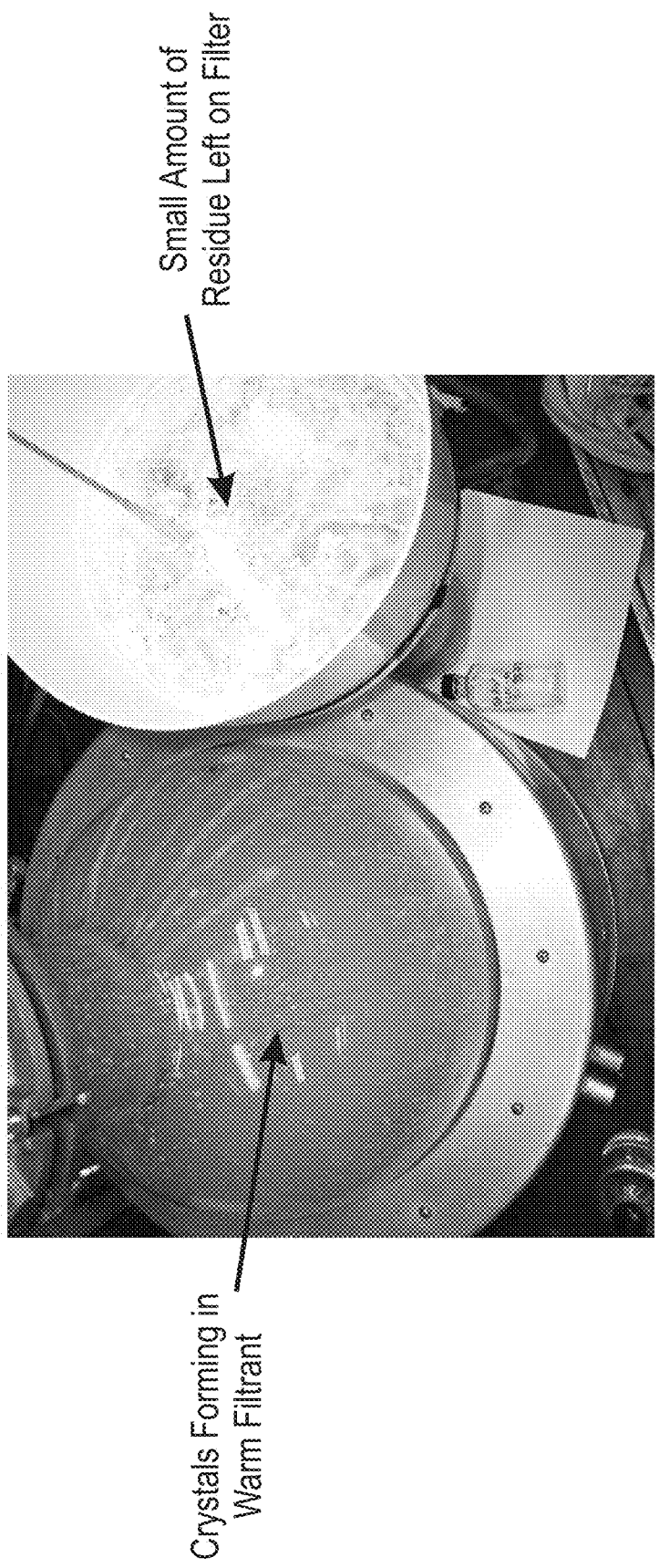
FIG. 2 is a photograph showing the results of a depolymerization reaction carried out with water contaminated PET input with the incorporation of the pre-reaction distillation process described herein (Example 2).

The presence of impurities in polyester inputs for the VolCat reaction has the potential to adverse effect the reaction rate of the reaction by affecting the performance of the organocatalyst. For example, impurities in the polyester input may (i) produce and increase in depolymerization times; (ii) partially inactive the organocatalyst resulting in reduced depolymerization of the input, and/or (iii) completely inactivate the organocatalyst. Where the organocatalyst is partially inactivated, unreacted polyester will be introduced into the product stream (FIG. 1). The removal of impurities from the input by the pre-reaction distillation alleviates the complications resulting from partial or incomplete depolymerization; thus, allowing the VolCat process to run smoothly and consistently (FIG. 2).

FIG. 1 shows that application of the VolCat process on water-contaminated dirty mixed color PET flake results in clogged filters due to incomplete depolymerization of the PET (Example 1). FIG. 2 shows that the incorporation of pre-reaction distillation to the same water-contaminated dirty mixed color PET flake results in significantly improved VolCat depolymerization (Example 2). The pre-reaction distillation produces very little residue resulting in improved filtration and purity of the reaction products.

Figure 3:
FIG. 3 is a photograph showing clean color PET flake before and after decolorization treatment with dichloromethane (DCM) (Example 3).
Figure 4A:
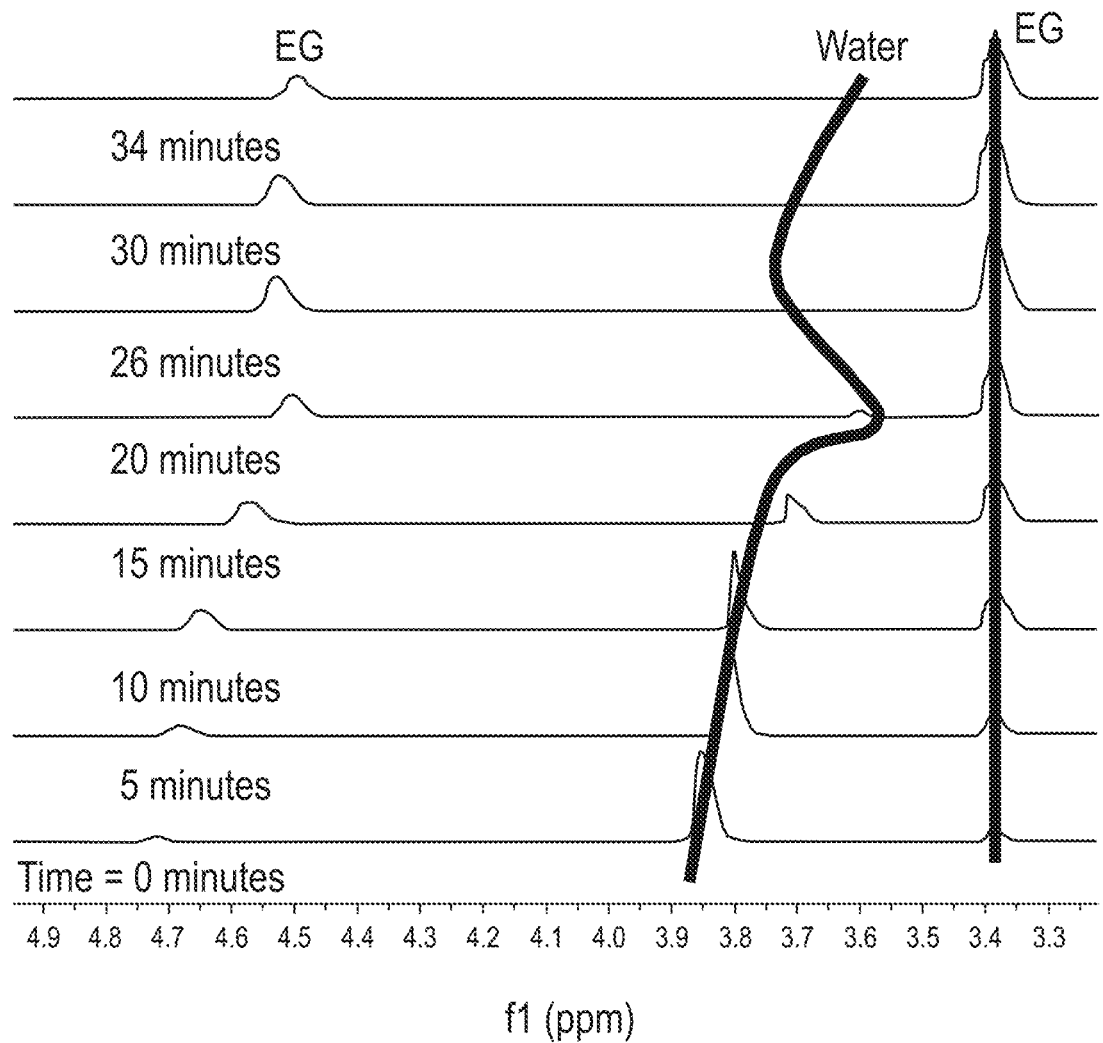
FIGS. 4A and 4B are H-NMR (d-DMSO) analytic results for water and ethylene glycol (EG) content from distillates obtained over the course of 34 minutes from wet dirty mixed color PET flake (Example 2).
Figure 4B:
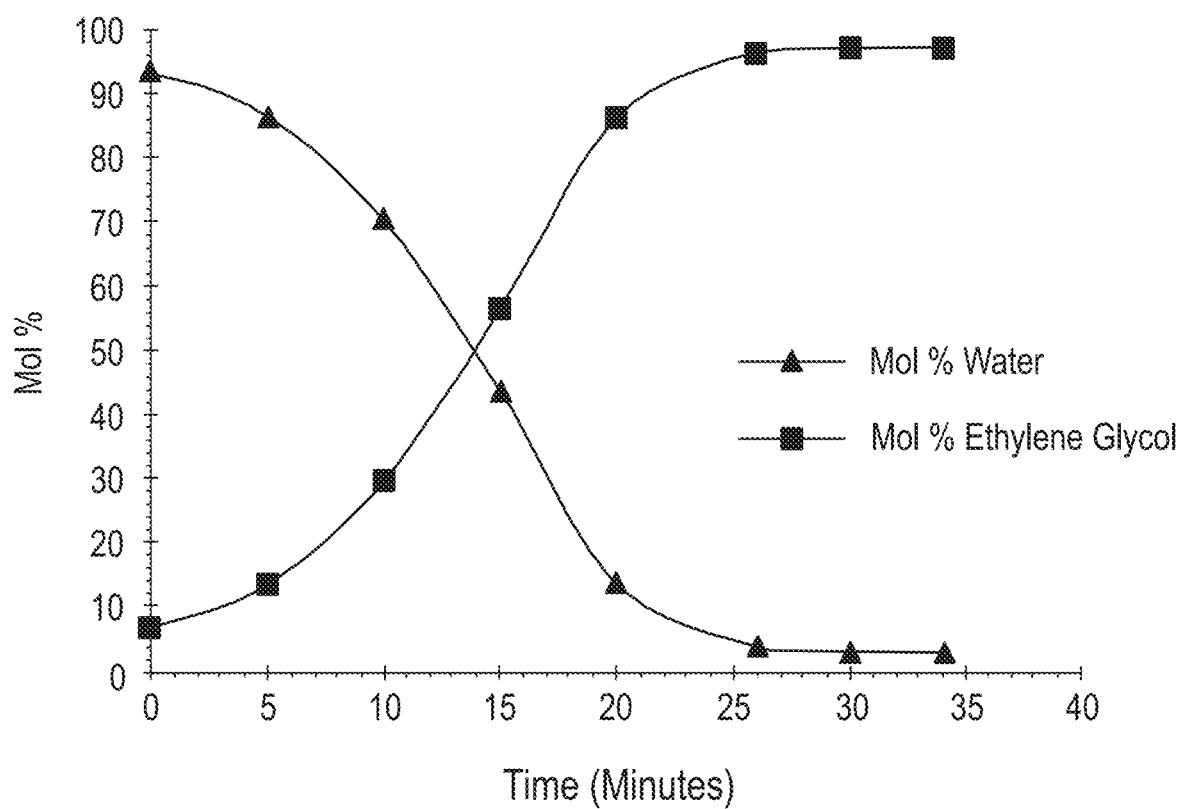

FIG. 3 shows the decolorization of clean color PET flake following treatment with DCM. FIGS. 4A and 4B show H-NMR analytic data for distillates obtained over a period of 34 minutes during pre-reaction distillation of wet dirty mixed color flake (Example 2). FIG. 4A shows the water and EG measurements for the distillates and FIG. 4B shows the stacked H-NMR data spectra for the distillates showing the mole fraction of residual water and EG over time. The data in FIGS. 4A and 4B show that the amount of water in the distillates decreases as the temperature rises in the reactor and that the amount of water in the samples was effectively removed by 25 minutes of heating.

Figure 5:
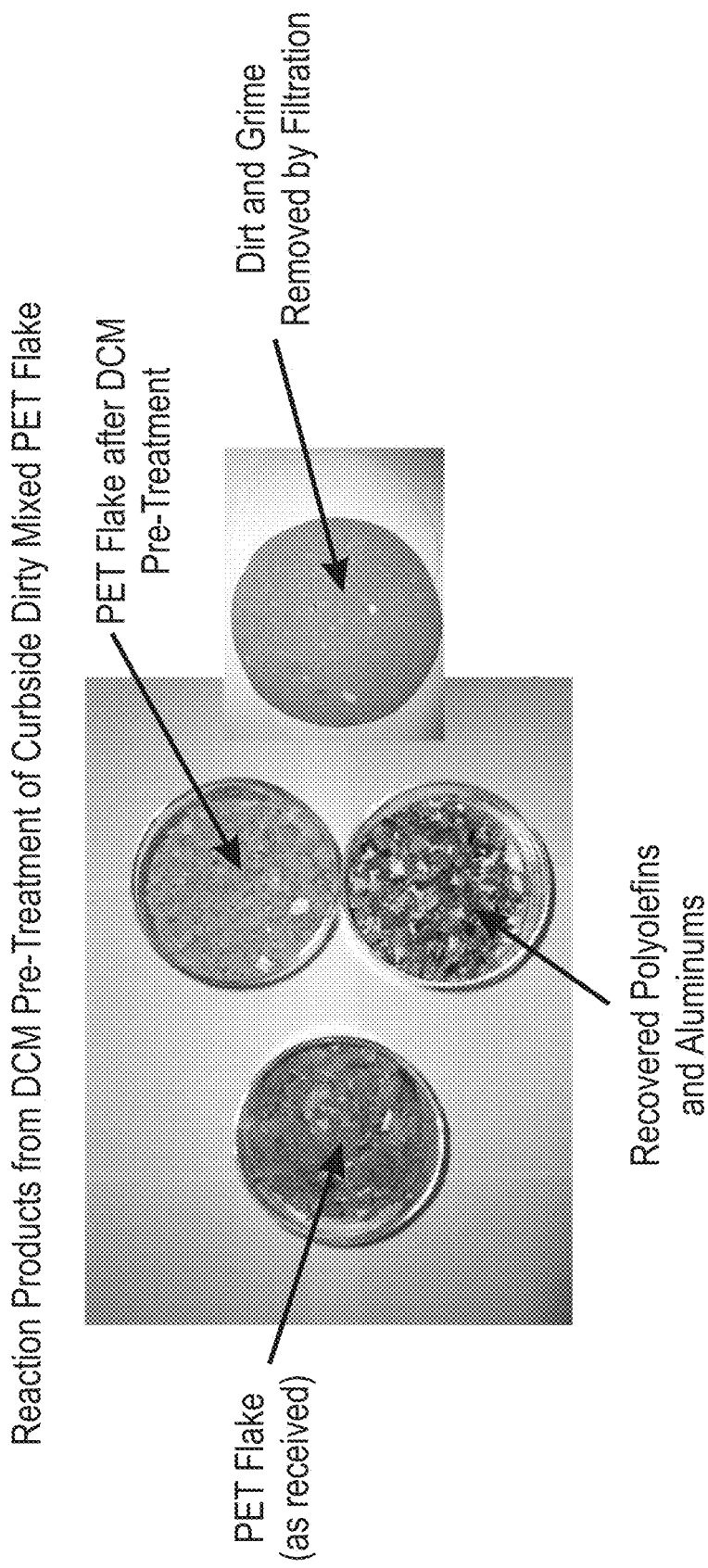
FIG. 5 is a photograph showing curbside dirty mixed PET flake before and after pre-reaction purification treatment with dichloromethane (DCM) (Example 4).
Figure 6:
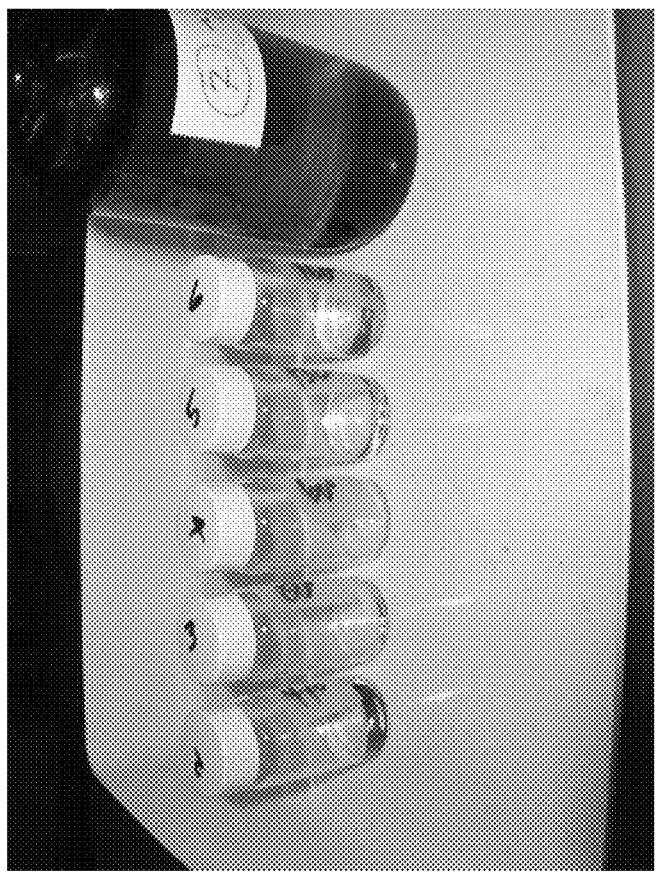
FIG. 6 is a photograph of five distillate fractions of DCM-treated curbside dirty mixed PET flake (Example 4).

FIG. 5 show curbside dirty mixed PET flake before and after treatment with DCM and FIG. 6 shows six distillate fractions taken from pre-reaction distillation of the same curbside dirty mixed PET flake (Example 4). TABLE 1 shows HPLC UV absorbance percentages ($\lambda=250$ nm) for the reaction products (the BHET and mother liquor) following the VolCat depolymerizations described in Examples 1 and 2. As shown in TABLE 1 and FIGS. 1 and 2, the reaction products obtained from the VolCat depolymerization of the dirty mixed PET flake that incorporate pre-reaction distillation (Example 2; FIG. 2) are purer and have a higher yield than the reaction products from the VolCat depolymerizations that do not include pre-reaction distillation (Example 1; FIG. 1). A higher proportion of the desired BHET and dimer products and less of the carboxylic acid hydrolysis product are seen in TABLE 1 for the sample produced using the pre-reaction distillation step (Example 2). TABLE 2 (Example 5) shows that the pre-reaction distillation has no discernable effect on the pore volume and porosity of VolCat monomeric or oligomeric diester reaction products. TABLE 2 further shows that VolCat reactions, with or without pre-reaction distillation, produce monomeric and/or oligomeric diester reaction products with higher pore volume and comparable porosity to commercially obtainable monomeric and/or oligomeric diester reaction products.

TABLE 1

| SAMPLE | | ACID | BHET | DIMER |
| --- | --- | --- | --- | --- |
| Example 1 | BHET | 2 | 90 | 8 |
| (no distillation) | Mother Liquor | 21 | 76 | 3 |
| Example 2 | BHET | 1 | 92 | 7 |
| (with distillation) | Mother Liquor | 14 | 84 | 2 |

Figure 7:
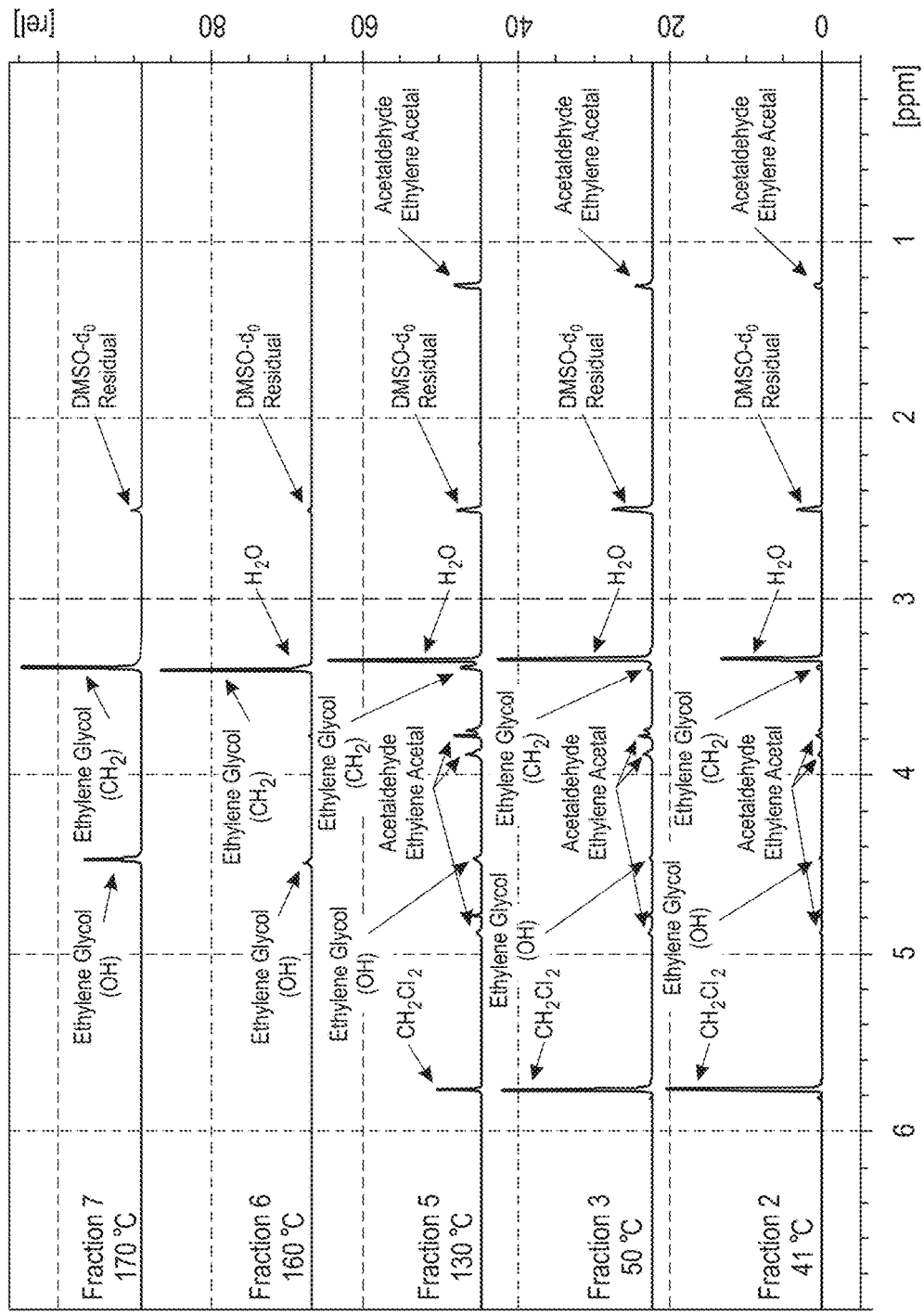
FIG. 7 are NMR results of the five distillate fractions of FIG. 6.

FIG. 7 shows stacked NMRs of the five distillate fractions from Example 4, which are shown in FIG. 6. The early fractions (Fractions 2 and 3) contain mostly DCM, acetaldehyde ethylene acetal, and water. By Fraction 5, which was collected at a temperature of 130° C., the undesirable acetaldehyde ethylene acetal and DCM are completely removed. By the time Fractions 6 and 7 were collected at temperatures of 160 and 170° C., respectively, the water was completely removed and the fractions were mainly unreacted EG.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

Example 1

Depolymerization Reaction Run with Water Contaminated Pet Input

A 1005 g dirty mixed color flake PET sample was used having visible water content residue remaining from a water-cooled chipping process. The PET and 4506 g of EG were added to an 8 L stainless steel Parr reactor with stirring, the Parr reactor attached to a closed off distillation column with pressure regulation at the terminus and an addition burette containing 26.3 g TEA and 25 g EG. The reaction was heated to 220° C. and the TEA/EG mixture was added by pressurization to 30 psi. The reaction was run at this temperature for 1.5 hours. The TEA was distilled off by first opening the valve to the distillation column, then lowering the pressure slowly to cause distillation. The distillation produced a biphasic liquid, which was found to be TEA with a significant amount of water; the total weight of the distilled sample measuring 46 g total. Additional distillation was carried out until a total of 118 g were recovered. The reaction solution was allowed to cool to 80-85° C. at which time filtration of the reaction solution with a filter aid was attempted even, but was not successful due to the pasty nature of the crystals that formed during the reaction process and could not be successfully resolubilized. The filtration was terminated after repeated attempts to scrape the pasty mass from the surface of the filter aid. The remaining solution was cooled further to allow crystallization. Besides the dirt on the filter cake, there was about 40 g of mainly polyolefins recovered as coagulated masses. The following day the slurry was broken up and a pasty mass was scraped from the filter cake surface, the pasty mass containing some product crystals and recovered polyolefin as shown in FIG. 1.

Example 2

Pre-Reaction Distillation and Depolymerization of Water Contaminated Pet Flake Input A 1004 g dirty mixed color flake PET sample was used having visible water content residue remaining from the water-cooled chipping process. The PET and 4500 g of EG were added to an 8 L stainless steel Parr reactor open to a distillation column connected to a Firestone valve having N2 flow, with stirring, and an addition burette containing 26.3 g TEA and 25 g EG. The reaction was heated to 220° C. while collecting distillate until the distillate temperature reached about 180° C. Distillate fractions were sampled over 34 minutes and analyzed by H-NMR in d-DMSO solvent to follow the disappearance of water (FIGS. 4A and 4B). The water in the samples was found to be effectively removed by 25 minutes of heating. To run the reaction, the valve to the column and the pressure regulator were closed and the TEA/EG mixture was added to the reaction by pressurization to 30 psi. The reaction was run at this temperature for 1.5 hours. The TEA was distilled off by first opening the valve to the distillation column, then lowering the pressure slowly to cause distillation. The distillation produced a monophasic liquid, which was found to be TEA with no discernable water. The reaction solution was allowed to cool to 80-85° C. and was easily filtered using a diatomaceous earth filter aid. Besides the dirt on the filter cake, there was about 41 g of sample made up primarily of polyolefins recovered as coagulated masses. This reaction sequence was followed two more times using the same filter aid with no difficulty in filtration. After the third run, crystals formed in the vessel after filtration through a filter aid, but no residue was apparent as shown in FIG. 2. The same filter aid that was used in FIG. 2 was used for the filtration of two subsequent reactions without difficulty.

Example 3

Pre-Reaction Distillation and Depolymerization of Clean Color Pet Flake Input 2.5 kg of clean color PET flakes were added to a 22 L reactor. 12 L of DCM was added to the reactor and stirred gently. The DCM took on a dark color almost immediately. Aliquots of the DCM were taken every hour for 6 hours then after 24 hours for analysis. After 24 hours the PET flake was filtered away from the DCM and sucked dry. FIG. 3 shows the PET flake before and after the DCM decolorization treatment.

1004 g of the pre-processed clean color PET flake and 4500 g of EG were added to an 8 L stainless steel Parr reactor open to a distillation column connected to a Firestone valve having N2 flow, with stirring, and an addition burette containing 53 g TEA and 25 g EG. The reaction was heated to 220° C. while collecting distillate until the distillate temperature reached about 180° C. The reactor took approximately 30 minutes to heat from ambient temperature to 180° C. Distillate fractions were collected at the following temperature intervals: 64.8° C., 130° C. (at which time the water started to distill), 165° C. (in two phases), and 180° C. To run the reaction, the valve to the distillation column and the pressure regulator were closed. When the reaction reached 220° C., the TEA/EG mixture was added by pressurization of the sample chamber to 30 psi. The reaction was run at this temperature for 1.5 hours. The TEA was distilled off by first opening the valve to the distillation column, then lowering the pressure slowly to cause distillation. The distillation produced a monophasic liquid, which was found to be TEA with no discernable water. The reaction solution was allowed to cool to 80-85° C. at which time the solution was easily filtered through a filter aid. The product filtration was easy, showing no residual unreacted flakes or paste. Crystallization of the polyester reaction product, BHET, proceeded as usual.

Example 4

Pre-Reaction Distillation and Depolymerization of Curbside Dirty Mixed Pet Flake Input 2.5 kg of dirty curbside dirty mixed PET flake was added to a 22 L glass reactor along with 12 L DCM and stirred gently at room temperature. The DCM took up a surprising amount of color immediately upon addition to the flake contained in the flask—even before stirring. Samples of DCM were taken at 1, 2, and 3 hours. The less dense material was skimmed from the surface of the liquid and found to be PE, PP, and aluminum film. The remaining PET flakes were filtered. Much of the dirt and grime that was originally on or in the dirty PET was released into the DCM liquid and was easily filtered from the liquid and the cleaned PET flakes easily recovered. There was very little colored material in the resultant product either as polyolefin or color remaining in the PET. A picture of a portion of the flake before and after this process is shown in FIG. 5.

The depolymerization process described in Example 3 was repeated here with the pre-processed curbside dirty mixed PET flake. The reaction was heated to 220° C. while collecting distillate until the distillate temperature reached about 170° C. Distillate fractions were collected at the following temperatures: 41° C., 50° C., 60° C., 130° C., 160° C., and 170° C. (FIG. 6) and NMR readings were taken of each of the fractions (FIG. 7). The reactor was then sealed off from the distillation column and the addition of catalyst, reaction conditions, and product recovery of BHET were carried out as usual.

Example 5

Monomer Product Porosity and Pore Volume

Porosity and pore volume measurements were calculated for BHET monomer products obtained from traditional VolCat depolymerization of PET and from Example 2 (VolCat depolymerization of PET with pre-reaction distillation). TABLE 2 shows the results of the test. Two Aldrich BHET monomers were tested concurrently and are included in TABLE 2 for commercial product comparison. The porosity and pore volume measurements were determined by mercury intrusion porosimetry performed in accordance with ASTM D 4404-10 where the samples were pre-degassed in a vacuum at 25° C. for 16 h at a contact t angle of 140° (Particle Testing Authority, 4356 Communications Dr., Norcross, GA 30093).

TABLE 2

|  | Aldrich Lot 56196PJ** | Aldrich Lot 56196PJ* | IBM Clean Color Flake | IBM Curbside Dirty Mixed Flake | IBM Clean Clear Flake | IBM Dirty Mixed Color Flake from Example 2 |
|---|---|---|---|---|---|---|
| Bulk density (g/cm3) | 1.1533 | 1.0057 | 0.5312 | 0.6970 | 0.4564 | 0.5358 |
| Apparent (skeletal) density (g/cm) | 1.45 | 2.92 | 1.57 | 3.29 | 1.42 | 1.49 |
| Pore volume (mL/g) | 0.1769 | 0.65 | 1.24 | 1.13 | 1.49 | 1.19 |
| Porosity (%) | 20.4 | 65.5 | 66.1 | 78.8 | 67.9 | 64.0 |

*Manufactured by Aldrich in 2008; porosity and pore volume tested concurrently with IBM samples.
**Manufactured by Aldrich in 2001; porosity and pore volume tested concurrently with IBM samples.

We claim:

1. A method comprising:
    distilling a material comprising a polyester to remove volatile impurities from the material;
    reacting the distilled material with an organocatalyst and an alcohol solvent in a chemical reactor; and
    recovering reaction products from the chemical reactor upon completion of the depolymerization, wherein the reaction products comprise (i) a monomeric or oligomeric diester from the polyester, (ii) the organocatalyst for reuse, and (iii) the alcohol solvent as an unreacted by-product of the depolymerization.

2. The method of claim 1, wherein the chemical reactor is a pressure reactor.

3. The method of claim 2, wherein the pressure reactor is an autoclave.

4. The method of claim 2, wherein the pressure reactor is an extrusion reactor.

5. The method of claim 1, wherein the chemical reactor is a non-pressurized reactor.

6. The method of claim 5, wherein the non-pressurized reactor is a round-bottom flask.

7. A method comprising:
    removing water from a material comprising a polyester by treating the material with a solvent that forms an azeotrope with water;
    distilling the material with distillation to remove volatile impurities from the material;
    reacting distilled material with an organocatalyst and an alcohol solvent in a chemical reactor to depolymerize the distilled material; and
    recovering reaction products from the chemical reactor upon completion of the depolymerization, wherein the reaction products comprise (i) a monomeric or oligomeric diester from the polyester, (ii) the organocatalyst for reuse, and (iii) the alcohol solvent as an unreacted by-product of the depolymerization.

8. The method of claim 7, wherein the chemical reactor is a pressure reactor.

9. The method of claim 8, wherein the pressure reactor is an autoclave.

10. The method of claim 8, wherein the pressure reactor is an extrusion reactor.

11. The method of claim 7, wherein the chemical reactor is a non-pressurized reactor.

12. The method of claim 11, wherein the non-pressurized reactor is a round-bottom flask.

13. A method comprising:
    treating a material comprising a polyethylene terephthalate (PET) with a distillation process to remove volatile impurities from the material;
    depolymerizing the distilled material with an amine organocatalyst and/or carboxylic acid salt of same and an alcohol solvent in a chemical reactor; and
    recovering reaction products from the chemical reactor upon completion of the depolymerization, wherein the reaction products comprise (i) bis(2-hydroxyethyl)terephthalate (BHET) as a monomeric diester of the PET, (ii) the amine organocatalyst for reuse, and (iii) any excess alcohol solvent.

14. The method of claim 13, wherein the chemical reactor is a pressure reactor.

15. The method of claim 14, wherein the pressure reactor is an autoclave.

16. The method of claim 14, wherein the pressure reactor is an extrusion reactor.

17. The method of claim 13, wherein the chemical reactor is a non-pressurized reactor.

18. The method of claim 17, wherein the non-pressurized reactor is a round-bottom flask.

* * * * *